United States Patent
Lennon et al.

(10) Patent No.: US 7,255,870 B2
(45) Date of Patent: *Aug. 14, 2007

(54) COMPOSITION CONTAINING A SEMICRYSTALLINE POLYMER, USES THEREOF, AND METHOD FOR MAKING

(75) Inventors: Paula Lennon, Lyons (FR); Raluca Lorant, Thiais (FR)

(73) Assignee: L'Oreal, Paris (FR)

( * ) Notice: Subject to any disclaimer, the term of this patent is extended or adjusted under 35 U.S.C. 154(b) by 452 days.

This patent is subject to a terminal disclaimer.

(21) Appl. No.: 10/347,338

(22) Filed: Jan. 21, 2003

(65) Prior Publication Data

US 2003/0165451 A1 Sep. 4, 2003

Related U.S. Application Data

(60) Provisional application No. 60/356,173, filed on Feb. 14, 2002, provisional application No. 60/355,824, filed on Feb. 13, 2002.

(30) Foreign Application Priority Data

| Jan. 24, 2002 | (FR) | 02 00883 |
| Jan. 24, 2002 | (FR) | 02 00885 |
| Feb. 25, 2002 | (FR) | 02 02357 |
| Feb. 25, 2002 | (FR) | 02 02358 |

(51) Int. Cl.
| A61K 8/06 | (2006.01) |
| A61K 8/33 | (2006.01) |
| A61K 8/36 | (2006.01) |
| A61K 8/37 | (2006.01) |
| A61K 8/92 | (2006.01) |
| A61K 47/06 | (2006.01) |
| A61K 47/08 | (2006.01) |
| A61K 47/10 | (2006.01) |
| A61K 47/12 | (2006.01) |
| A61K 47/14 | (2006.01) |
| A61K 47/44 | (2006.01) |
| A61Q 1/14 | (2006.01) |
| A61Q 5/00 | (2006.01) |
| A61Q 19/00 | (2006.01) |
| A61Q 99/00 | (2006.01) |

(52) U.S. Cl. .................. 424/401; 424/63; 424/64; 424/70.11; 424/70.12; 424/70.16; 424/70.17; 424/70.19; 424/78.03; 514/772; 514/772.3; 514/772.6; 514/785; 514/844; 514/880; 514/937; 504/363; 510/136

(58) Field of Classification Search ............ 424/401, 424/70.11, 70.15, 70.16, 70.17, 78.03, 78.16, 424/78.18, 78.24, 59, 78.02, 63, 64, 70.12, 424/70.19; 514/844, 846, 937, 939, 772, 514/772.3, 772.6, 785, 880; 504/358, 363; 510/136

See application file for complete search history.

(56) References Cited

U.S. PATENT DOCUMENTS

| 4,057,622 A | 11/1977 | Hase et al. |
| 4,057,623 A | 11/1977 | Hase et al. |
| 5,156,911 A * | 10/1992 | Stewart ............... 428/355 AC |
| 5,302,380 A | 4/1994 | Castrogiovanni et al. |
| 5,519,063 A | 5/1996 | Mondet et al. |
| 5,593,680 A * | 1/1997 | Bara et al. .................. 424/401 |
| 5,736,125 A | 4/1998 | Morawsky et al. |
| 5,958,431 A * | 9/1999 | Brancq et al. .............. 424/401 |
| 6,180,123 B1 | 1/2001 | Mondet |
| 6,395,285 B1 * | 5/2002 | Lorant ....................... 424/401 |
| 6,946,518 B2 | 9/2005 | De La Poterie |
| 6,949,504 B2 | 9/2005 | Mondet et al. |
| 7,129,276 B2 * | 10/2006 | Ferrari ..................... 514/772.3 |
| 2001/0018484 A1 | 8/2001 | Bitler et al. |
| 2005/0175560 A9 * | 8/2005 | Ferrari ........................ 424/63 |

FOREIGN PATENT DOCUMENTS

| DE | 19523478 | 12/1996 |
| DE | 19524210 | 1/1997 |
| EP | 0 951 897 | 10/1999 |
| EP | 1 034 776 | 9/2000 |
| EP | 1 163 898 | 12/2001 |
| EP | 1 262 164 | 12/2002 |
| WO | WO 93/01797 | 2/1993 |
| WO | WO 01/19333 | 3/2001 |

OTHER PUBLICATIONS

U.S. Appl. No. 60/294,977, filed Jun. 4, 2001.*
U.S. Appl. No. 11/012,332, filed Dec. 16, 2004, Charbit.
B. Boutevin, et al., "Study of morphological and mechanical properties of PP/PBT blends," Polymer Bulletin, vol. 34, No. 1, Jan. 1995, pp. 117-123.

(Continued)

*Primary Examiner*—John Pak
(74) *Attorney, Agent, or Firm*—Oblon, Spivak, McClelland, Maier & Neustadt, P.C.

(57) ABSTRACT

A composition containing an aqueous phase dispersed in an oily phase, at least one emulsifier with an HLB value ranging from 1 to 8, at least one organic powder, and, in the oily phase at least one semicrystalline polymer with organic structure that is solid at room temperature and that has a melting point of less than 70° C., the said polymer comprising a) a polymer skeleton and b) at least one crystallizable organic side chain and/or at least one crystallizable organic sequence forming part of the said polymer skeleton, the polymer having a number-average molecular weight of greater than 2,000. This composition can especially constitute a cosmetic cream, having a very pleasant texture when applied to the skin, or a stick, especially a makeup-removing stick.

30 Claims, No Drawings

OTHER PUBLICATIONS

Pratima Rangarajan, et al., "Morphology of Semicrystalline Block Copolymers of Ethylene-(Ethylene-alt-propylene)," Macromolecules, vol. 26, No. 17, Aug. 16, 1993, pp. 4640-4645.

D. Richter, et al., "Polymer Aggregates with Crystalline Cores: The System Polyethylene-Poly(ethylenepropylene)," Macromolecules, vol. 30, No. 4, Feb. 24, 1997, pp. 1053-1068.

I. W. Hamley, "Crystallization in Block Copolymers," Advances in Polymer Science, vol. 148, 1999, pp. 113-137.

Shuichi Nojima, et al., "Melting Behavior of Poly($\epsilon$-caprolactone)-block-Polybutadiene Copolymers," Macromolecules, vol. 32, No. 11, Jun. 1, 1999, pp. 3727-3734.

* cited by examiner

COMPOSITION CONTAINING A SEMICRYSTALLINE POLYMER, USES THEREOF, AND METHOD FOR MAKING

REFERENCE TO PRIOR APPLICATIONS

This application claims priority to U.S. provisional applications No. 60/355,824, filed Feb. 13, 2002, and No. 60/356,173, filed Feb. 14, 2002, and to French patent applications 0200883 filed Jan. 24, 2002, 0202357 filed Feb. 25, 2002, 0200885 filed Jan. 24, 2002, and 0202358 filed Feb. 25, 2002, all of which are expressly incorporated herein by reference.

SUMMARY OF THE INVENTION

The present invention relates to a composition, preferably in the form of a water-in-oil (W/O) emulsion, the composition containing an emulsifier, an organic powder and a certain type of polymer in the oily phase, and to its uses, especially in cosmetics or dermatology.

In a preferred embodiment the present invention relates to a composition preferably in the form of a water-in-oil emulsion, comprising an aqueous phase dispersed in an oily phase, containing at least one emulsifier with an HLB value ranging from 1 to 8, at least one organic powder, and, in the oily phase, at least one semicrystalline polymer with organic structure that is solid at room temperature and that has a melting point of less than 70° C., the polymer comprising a) a polymer skeleton and b) at least one crystallizable organic side chain and/or a crystallizable organic sequence forming part of the said polymer skeleton, the polymer having a number-average molecular mass (weight) of greater than 2,000.

The invention composition can especially constitute a cosmetic cream, having a very pleasant texture when applied to the skin, or a stick, especially a makeup-removing stick.

Other embodiments, attributes, etc. of the present invention will become clear from a full appreciation of the following description thereof.

BACKGROUND OF THE INVENTION

It is common practice in cosmetics or dermatology to use compositions consisting of a water-in-oil (W/O) emulsion comprising an aqueous phase dispersed in an oily phase. These emulsions can constitute creams, a cream being, in the fields under consideration, malleable and deformable products, as opposed to solid compositions. W/O emulsions comprise an oily continuous phase and thus make it possible to form at the surface of the skin a lipid film that prevents transepidermal water loss and protects the skin against external attack. These emulsions are particularly suitable for protecting and nourishing the skin, and in particular for treating dry skin. In addition, the lipid film formed at the surface of the skin may also increase the remanence of sunscreens. These emulsions also have the advantage of allowing the protection and transport of oxidation-sensitive hydrophilic active materials.

However, W/O emulsions have the drawback of giving a relatively greasy feel when applied to the skin, due to the fact that the oily phase is the external phase. Thus, these emulsions are generally used for dry skin, since they are too greasy to be used for greasy skin. Furthermore, W/O emulsions give no sensation of freshness and are generally too rich in oils to be used during summer or in hot countries.

Moreover, W/O emulsions have stability problems, especially when there is a large amount of aqueous phase: the drops of aqueous phase have a tendency to aggregate and to form lumps that are visible under a microscope. This aggregation is harmful to the stability of the emulsions; firstly, it promotes creaming or sedimentation of the fluid systems, and secondly the coalescence of the drops leads to the appearance of water regions, i.e. drops of aqueous phase larger than 50 microns. To stabilize these emulsions, it is often necessary to use a large proportion of emulsifiers and/or to introduce a certain amount of consistency factors, such as waxes. However, these consistency factors contribute towards accentuating the cosmetic defects (sticky and greasy effect) of the W/O emulsions, resulting in the production of compositions that are often heavy. Moreover, in the presence of these consistency factors, it is difficult to obtain fluid emulsions because these factors thicken the emulsions. In addition, if the amount of emulsifier in these emulsions is increased greatly to overcome their instability, the emulsions obtained may prove to be irritant towards certain skin types, especially sensitive skin.

Furthermore, for W/O compositions intended for removing makeup, the presence of a large amount of waxes reduces the properties of the compositions, especially of those intended for removing makeup from the skin, since the presence of waxes makes it difficult to remove the makeup remover when it is wiped or when it is rinsed (poor rinsability).

There is thus still a need for a W/O emulsion, which may especially be in cream form or in solid form, which does not have the drawbacks encountered with those known hitherto, in particular for an emulsion with a light and fresh feel, and which has good stability, even in the absence of the usual consistency factors of the oily phase, and especially even in the absence of waxes, even if it is desired to obtain a composition in solid form.

DETAILED DESCRIPTION OF THE INVENTION

Surprisingly, the inventors have found that the use of certain polymers in combination with one or more organic powders makes it possible to structure, even in the absence of wax, the oily phases of W/O emulsions containing an emulsifier of defined HLB, and leading to a composition that gives a non-sticky and fresh deposit.

For the purposes of the present application, the expression "oily phase" means a fatty phase that is liquid at room temperature (25° C.) and atmospheric pressure (760 mm Hg). The oily phase is preferably composed of one or more mutually compatible fatty substances that are liquid at room temperature, also known as oils. This oily phase is preferably macroscopically homogeneous.

More specifically, one subject of the invention is a composition, that preferably is suitable for topical application, comprising an aqueous phase dispersed in an oily phase, characterized in that it contains at least one organic powder and at least one emulsifier with an HLB value of from 1 to 8, and in that the oily phase comprises at least one semicrystalline polymer that is solid at room temperature and that has a melting point of less than 70° C., the polymer comprising a) a polymer skeleton and b) at least one crystallizable organic side chain and/or at least one crystallizable organic sequence forming part of the polymer skeleton, the polymer having a number-average molecular mass (weight) of greater than 2,000.

In the present patent application, the expression "room temperature" means a temperature of 25° C.

The invention compositions containing semicrystalline polymers include creams that have very fondant textures with excellent spreading on the skin. It is believed, without being held to a particular theory, that the rheological properties of these semicrystalline polymers allow fluidization due to the shear effect during application to the skin. In addition to this, these polymers are advantageous on account of their capacity to change as a function of the temperature of the skin. Specifically, the semicrystalline polymer changes state as a function of the temperature of the skin and the temperature of the environment. When the temperature is below the melting point of the polymer, the polymer chains are rigid and the texture of the composition containing it is more compact and similar to that of a balm. When the temperature increases, the polymer chains relax and the texture of the composition becomes softer. The texture thus depends on the application temperature, and thus, the cream which appears to be compact in the jar may in fact prove to be very soft when applied to the skin.

In addition, in view of the combination of one or more semicrystalline polymers and organic powders, the compositions according to the invention have the advantage of having a pleasant texture, with a silky feel and a satiny but non-glossy final effect. In addition, the compositions allow the complexion to be made uniform and to protect the skin against attack (cold, wind or heat). Thus, after application to the skin, the compositions according to the invention constitute a protection against attack and adapt to the climate.

Moreover, when the composition according to the invention is in solid form, it simultaneously has the desired rigidity qualities so that the solid composition does not break, and sufficient transfer properties so that the product gives a good deposit on the skin and, in the case of makeup-removing compositions, allows good makeup removal and/or cleansing of the skin.

Since in one preferred embodiment the composition according to the invention is intended for topical application, especially to the skin, the lips or the integuments, it preferably comprises a physiologically acceptable medium. The expression "physiologically acceptable medium" means herein a non-toxic medium that may be applied to the skin (including the inside of the eyelids), the lips, the nails or the hair of human beings. The composition of the invention may especially constitute a cosmetic or dermatological composition.

The form of the invention composition is not limited and includes for example a cream or an ointment, i.e. a soft product as opposed to a solid product such as a stick. Of course, sticks, etc., are also included. A preferred cream has a viscosity at room temperature (about 25° C.) ranging from about 2 to 250 poises, i.e. 0.2 to 25 Pa·s, preferably from about 5 to 240 poises, i.e. 0.5 to 24 Pa·s, and better still 50 to 200 poises, i.e. 5 to 20 Pa·s, this viscosity being measured with a Rheomat 180 machine.

According to another embodiment, the composition of the invention may be solid and may especially constitute a stick, and in particular a makeup-removing stick. For the purposes of the present invention, the expression "solid composition" means any composition that does not flow under its own weight, having a hardness as defined below (shear strength of 100 to 350 gf).

Semicrystalline Polymers

For the purposes of the invention, the term "semicrystalline polymer" means polymers comprising a crystallizable portion, pendent chain or sequence in the skeleton, and an amorphous portion in the skeleton, and having a first-order reversible temperature of phase change, in particular of melting (solid-liquid transition). For the purposes of the invention, the term "polymers" means compounds comprising at least 2 repeating units, preferably at least 3 repeating units and more especially at least 10 repeating units. When the crystallizable portion is a sequence of the polymer skeleton, the chemical nature of this crystallizable sequence is different from that of the amorphous sequences; the semicrystalline polymer is in this case a block polymer, for example of the diblock, triblock or multiblock type.

Advantageously, the semicrystalline polymer(s) of the composition of the invention has (have) a number-average molecular mass (weight) $\overline{M}n$ of greater than or equal to 2,000, ranging, for example, from 2,000 to 800,000, preferably from 3,000 to 500,000, for example from 4,000 to 150,000 and better still from 4,000 to 99,000.

In the composition according to the invention, the semicrystalline polymers are preferably soluble in the oily phase to at least 1% by weight, at a temperature above their melting point. Beyond the crystallizable chains or sequences, the polymer sequences are amorphous. For the purposes of the invention, the expression "crystallizable chain or sequence" means a chain or sequence which, if it was alone, would pass from the amorphous state to the crystalline state, reversibly, depending on whether it is above or below the melting point. For the purposes of the invention, a chain is a group of atoms that is pendent or lateral relative to the polymer skeleton. A sequence is a group of atoms belonging to the skeleton, this group constituting one of the repeating units of the polymer.

Preferably, the polymer skeleton of the semicrystalline polymers is soluble in the oily phase.

Preferably, the semicrystalline polymers used in the composition of the invention have a melting point Tm of less than 70° C. (25° C. $\leq$Tm<70° C.), preferably less than or equal to than 60° C., for example from 30° C. to 60° C. (30° C. $\leq$Tm$\leq$60° C.), this temperature preferably being at least equal to the temperature of the keratinous support that is to receive the composition according to the invention. When the composition constitutes a non-solid product and especially a cream, the melting point is preferably less than 60° C. and still less than 50° C. (30° C. $\leq$Tm<50° C.). The melting point may be measured by any known method and in particular using a differential scanning calorimeter (DSC).

Preferably, the crystallizable sequences or chains of the semicrystalline polymers represent at least 30% of the total weight of each polymer and better still at least 40%. The semicrystalline polymers containing crystallizable sequences used according to the invention are preferably block or multiblock polymers. They may be obtained by polymerization of a monomer containing reactive (or ethylenic) double bonds or by polycondensation. When the polymers of the invention are polymers containing crystallizable side chains, they are advantageously in random form.

Preferably, the semicrystalline polymers of the invention are of synthetic origin. In addition, they preferably do not comprise a polysaccharide skeleton.

Semicrystalline polymers that may be used in the invention include:

1. block copolymers of polyolefins of controlled crystallization, the monomers of which are described in document EP-A-951 897;
2. polycondensates and especially aliphatic or aromatic polyester polycondensates and aliphatic/aromatic copolyesters;

3. polymers (homopolymers or copolymers) bearing at least one crystallizable side chain, and polymers (homopolymers or copolymers) bearing in the skeleton at least one crystallizable sequence, for instance those described in document U.S. Pat. No. 5,156,911;
4. polymers (homopolymers or copolymers) bearing at least one crystallizable side chain containing one (or more) fluoro group(s), as described in document WO-A-01/19333;
5. and mixtures thereof.

In the last two cases (3 and 4), the crystallizable sequence(s) or side chain(s) is(are) hydrophobic.

Examples of crystalline polymers containing crystallizable side chains or bearing in the skeleton at least one crystallizable sequence (case 3 indicated above) are described more particularly hereinbelow.

A) Semicrystalline Polymers Containing Crystallizable Side Chains

Examples may be found, and mention may be made in particular of those described in documents U.S. Pat. No. 5,156,911 and WO-A-01/19333. They are homopolymers or copolymers comprising from 50% to 100% by weight of units resulting from the polymerization of one or more monomers bearing crystallizable hydrophobic side chain(s). These polymers are of any nature provided that they meet the conditions indicated below with, in particular, the characteristic of being soluble or dispersible in the oily phase, by heating above their melting point Tm. They may result:

from the polymerization, especially free-radical polymerization, of one or more monomers containing reactive or ethylenic double bonds with respect to a polymerization, i.e. a vinyl, (meth)acrylic or allylic group;

from the polycondensation of one or more monomers bearing co-reactive groups (carboxylic acid, sulphonic acid, alcohol, amine or isocyanate), such as, for example, polyesters, polyurethanes, polyethers, polyureas and polyamides.

a) In general, the crystallizable units (chains or sequences) of the semicrystalline polymers according to the invention are obtained from monomer(s) containing crystallizable sequence(s) or chain(s), used for the manufacture of the semicrystalline polymers. These polymers are chosen especially from homopolymers and copolymers resulting from the polymerization of at least one monomer containing crystallizable chain(s) which may be represented by the formula X:

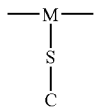

in which M represents an atom of the polymer skeleton, S represents a spacer and C represents a crystallizable group.

The crystallizable chains "—S—C" may be aliphatic or aromatic, and optionally fluorinated or perfluorinated. "S" especially represents a linear or branched or cyclic group $(CH_2)_n$ or $(CH_2CH_2O)_n$ or $(CH_2O)$, n being an integer ranging from 0 to 22. Preferably, "S" is a linear group. Preferably, "S" and "C" are different.

When the crystallizable chains are aliphatic (alkyl) chains, they comprise at least 11 carbon atoms and not more than 40 carbon atoms and better still not more than 24 carbon atoms. They are especially alkyl chains containing at least 12 carbon atoms, and are preferably alkyl chains containing from 14 to 24 carbon atoms ($C_{14}$-$C_{24}$). They may be hydrocarbon-based alkyl chains (carbon and hydrogen atoms) or fluoroalkyl or perfluoroalkyl chains (carbon atoms, fluorine atoms and possibly hydrogen atoms). When they are fluoroalkyl or perfluoroalkyl chains, they comprise at least 11 carbon atoms, at least 6 carbon atoms of which are fluorinated. Monomers having an alkyl chain containing at least 14 carbon atoms provide the resulting polymers with structuring of the fatty phase by crystallization, which is not the case with carbon-based alkyl chains containing less than 14 carbon atoms.

Examples of semicrystalline polymers or copolymers containing crystallizable chain(s) include those resulting from the polymerization of at least one monomer containing a crystallizable chain chosen from saturated $C_{14}$-$C_{24}$ alkyl (meth)acrylates ("$C_{14}$-$C_{24}$" means that the alkyl group contains from 14 to 24 carbon atoms); $C_{11}$-$C_{15}$ is perfluoroalkyl (meth)acrylates (alkyl group with 11 to 15 carbon atoms); $C_{14}$ to $C_{24}$ N-alkyl(meth)acrylamides with or without a fluorine atom (alkyl group with 14 to 24 carbon atoms); vinyl esters containing $C_{14}$ to $C_{24}$ alkyl or perfluoroalkyl chains (alkyl group with 14 to 24 carbon atoms), a perfluoroalkyl chain containing at least 6 fluorine atoms; vinyl ethers containing $C_{14}$ to $C_{24}$ alkyl or perfluoroalkyl chains (alkyl group with 14 to 24 carbon atoms), a perfluoroalkyl chain containing at least 6 fluorine atoms; $C_{14}$ to $C_{24}$ α-olefins (alkyl group with 14 to 24 carbon atoms) such as, for example, octadecene; $C_{14}$ to $C_{24}$ para-alkylstyrenes (alkyl group with 14 to 24 carbon atoms), and mixtures thereof.

For the purposes of the invention, the term "alkyl" means a saturated group especially containing from 8 to 24 carbon atoms ($C_8$ to $C_{24}$), except where specifically mentioned, and better still from 14 to 24 carbon atoms ($C_{14}$ to $C_{24}$).

When the polymers result from a polycondensation, the hydrocarbon-based and/or fluorinated crystallizable chains as defined above are borne by a monomer that may be a diacid, a diol, a diamine or a diisocyanate.

When the polymers used in the composition of the invention are copolymers, they also contain from 0 to 50% of groups Y or Z resulting from the copolymerization:

α) With Y which is a polar or non-polar monomer or a mixture of the two:

When Y is a polar monomer, it is either a monomer bearing polyoxyalkylenated (especially oxyethylenated and/or oxypropylenated) groups, a hydroxyalkyl (meth)acrylate, for instance hydroxyethyl acrylate, (meth)acrylamide, an N-alkyl(meth)acrylamide, an N,N-dialkyl(meth)acrylamide such as, for example, N,N-diisopropylacrylamide or N-vinylpyrrolidone (NVP), N-vinylcaprolactam, or a monomer bearing at least one carboxylic acid group, for instance (meth) acrylic acids, crotonic acid, itaconic acid, maleic acid or fumaric acid or bearing a carboxylic acid anhydride group, for instance maleic anhydride, and mixtures thereof.

When Y is a non-polar monomer, it may be an ester of the linear, branched or cyclic alkyl (meth)acrylate type, a vinyl ester, an alkyl vinyl ether, an α-olefin, styrene or styrene substituted with an alkyl group containing from 1 to 10 carbon atoms ($C_1$ to $C_{10}$), for instance α-methylstyrene, or a macromonomer of the polyorganosiloxane type containing vinylic unsaturation.

β) With Z which is a polar monomer or a mixture of polar monomers, Z having the same definition as the "polar Y" defined above.

Preferably, the semicrystalline polymers containing a crystallizable side chain are chosen from alkyl (meth)acrylate or alkyl(meth)acrylamide homopolymers with an alkyl group as defined above, and especially of $C_{14}$-$C_{24}$; the copolymers of these monomers with a hydrophilic monomer preferably different in nature from (meth)acrylic acid; and mixtures thereof. They may be, for example, copolymers, copolymers of alkyl (meth)acrylate or of alkyl(meth)acrylamide with a $C_{14}$ to $C_{24}$ alkyl group, with N-vinylpyrrolidone, hydroxyethyl (meth)acrylate or acrylic acid; or mixtures thereof.

B) Polymers Bearing in the Skeleton at Least one Crystallizable Sequence:

These are again polymers that are soluble or dispersible in the oily phase by heating above their melting point Tm. These polymers are preferably block copolymers consisting of at least two sequences of different chemical nature, one of which is crystallizable.

The following may preferably be used:

1) the polymers defined in document U.S. Pat. No. 5,156,911;

2) block copolymers of olefin or of cycloolefin containing a crystallizable chain, for instance those derived from the block polymerization of:

cyclobutene, cyclohexene, cyclooctene, norbornene (i.e. bicyclo[2.2.1]hept-2-ene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydronaphthalene, dicyclopentadiene, or mixtures thereof;

with ethylene, propylene, 1-butene, 3-methyl-1-butene, 1-hexene, 4-methyl-1-pentene, 1-octene, 1-decene or 1-eicosene, or mixtures thereof.

These block copolymers preferably include (ethylene/norbornene) block copolymers and (ethylene/propylene/ethylidenenorbornene) block terpolymers. Those resulting from the block copolymerization of at least 2 $C_2$-$C_{16}$ and better still $C_2$-$C_{12}$ α-olefins, such as those mentioned above and in particular block bipolymers of ethylene and of 1-octene, may also be used.

3) Copolymers containing at least one crystallizable sequence, the rest of the copolymer being amorphous (at room temperature). These copolymers may also have two crystallizable sequences of different chemical nature. The preferred copolymers are those simultaneously containing at room temperature a crystallizable sequence and an amorphous sequence that is both hydrophobic and lipophilic, sequentially distributed; examples that may be mentioned include polymers containing one of the crystallizable sequences below and one of the amorphous sequences below:

Naturally crystallizable sequence: a) polyester, for instance poly(alkylene terephthalate), b) polyolefin, for instance polyethylenes or polypropylenes.

Amorphous and lipophilic sequence, for instance amorphous polyolefins or amorphous copoly(olefins) such as poly(isobutylene), hydrogenated polybutadiene or hydrogenated poly(isoprene).

Examples of such copolymers containing a crystallizable sequence and an amorphous sequence include:

α) Poly(ε-caprolactone)-b-poly(butadiene) block copolymers, preferably used in hydrogenated form, such as those described in the article "Melting behavior of poly(-caprolactone)-block-polybutadiene copolymers" by S. Nojima, Macromolecules, 32,3727-3734 (1999).

β) Block or multiblock hydrogenated poly(butylene terephthalate)-b-poly(isoprene) block copolymers, mentioned in the article "Study of morphological and mechanical properties of PP/PBT" by B. Boutevin et al., Polymer Bulletin, 34,117-123 (1995).

γ) The poly(ethylene)-b-copoly(ethylene/propylene) block copolymers mentioned in the articles "Morphology of semicrystalline block copolymers of ethylene-(ethylene-alt-propylene)" by P. Rangarajan et al., Macromolecules, 26,4640-4645 (1993), and "Polymer aggregates with crystalline cores: the system poly(ethylene)-poly(ethylene-propylene)" by P. Richter et al., Macromolecules, 30,1053-1068 (1997).

δ) The poly(ethylene)-b-poly(ethylethylene) block copolymers mentioned in the general article "Crystallization in block copolymers" by I. W. Hamley, Advances in Polymer Science, vol. 148,113-137 (1999).

The semicrystalline polymers in the composition of the invention may be non-crosslinked or partially crosslinked, provided preferably that the degree of crosslinking does not harm their dissolution or dispersion in the oily phase by heating above their melting point. This may then be a chemical crosslinking, by reaction with a multifunctional monomer during the polymerization. It may also be a physical crosslinking which may then be due either to the establishment of bonds of hydrogen type or dipolar type between groups borne by the polymer, such as, for example, the dipolar interactions between carboxylate ionomers, these interactions being of small amount and borne by the polymer skeleton; or to a phase separation between the crystallizable sequences and the amorphous sequences borne by the polymer.

Preferably, the semicrystalline polymers in the composition according to the invention are non-crosslinked.

According to one particular embodiment of the invention, the polymer is chosen from copolymers resulting from the polymerization of at least one monomer containing a crystallizable chain chosen from saturated $C_{14}$-$C_{24}$ alkyl (meth)acrylates, $C_{11}$-$C_{15}$ perfluoroalkyl (meth)acrylates, $C_{14}$ to $C_{24}$ N-alkyl(meth)acrylamides with or without a fluorine atom, vinyl esters containing $C_{14}$ to $C_{24}$ alkyl or perfluoroalkyl chains, $C_{14}$ to $C_{24}$ α-olefins, para-alkylstyrenes with an alkyl group containing from 12 to 24 carbon atoms, with at least one optionally fluorinated $C_1$ to $C_{10}$ monocarboxylic acid ester or amide, which may be represented by the following formula:

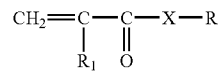

in which $R_1$ is H or $CH_3$, R represents an optionally fluorinated $C_1$-$C_{10}$ alkyl group and X represents O, NH or $NR_2$, in which $R_2$ represents an optionally fluorinated $C_1$-$C_{10}$ alkyl group.

According to one more particular embodiment of the invention, the polymer is derived from a monomer containing a crystallizable chain chosen from saturated $C_{14}$-$C_{22}$ alkyl (meth)acrylates.

Examples of semicrystalline polymers that may be used in the composition according to the invention include the Intelimer® products from the company Landec described in the brochure "Intelimer® polymers". These polymers are in solid form at room temperature (25° C.). They bear crystallizable side chains and have the above formula X. Mention may be made especially of "Landec IP22" having a melting point Tm of 56° C., which is an impermeable, non-sticky product that is viscous at room temperature.

The semicrystalline polymers described in Examples 3, 4, 5, 7 and 9 of document U.S. Pat. No. 5,156,911, resulting from the copolymerization of acrylic acid and of a $C_5$ to $C_{16}$ alkyl (meth)acrylate having a Tm ranging from 20° C. to 35° C. may also be used, and more particularly those resulting from the copolymerization:
- of acrylic acid, of hexadecyl acrylate and of isodecyl acrylate in a 1/16/3 ratio;
- of acrylic acid and of pentadecyl acrylate in a 1/19 ratio;
- of acrylic acid, of hexadecyl acrylate and of ethyl acrylate in a 2.5/76.5/20 ratio;
- of acrylic acid, of hexadecyl acrylate and of methyl acrylate in a 5/85/10 ratio;
- of acrylic acid and of polyoctadecyl methacrylate in a 2.5/97.5 ratio.

The polymer "Structure O" sold by the company National Starch, such as the product described in document U.S. Pat. No. 5,736,125, with a Tm of 44° C., and also semicrystalline polymers containing crystallizable pendent chains comprising fluorinated groups, as described in Examples 1, 4, 6, 7 and 8 of document WO-A-01/19333, may also be used.

The semicrystalline polymers obtained by copolymerization of stearyl acrylate and of acrylic acid or of NVP, as described in document U.S. Pat. No. 5,519,063 or EP-A-0550745, and more especially those described in the polymer preparation examples 1 and 2 below, with a melting point of 40° C. and 38° C., respectively, may also be used.

The semicrystalline polymers obtained by copolymerization of behenyl acrylate and of acrylic acid or of NVP, as described in documents U.S. Pat. No. 5,519,063 and EP-A-0550745, and more especially those described in the polymer preparation examples 3 and 4 below, with a melting point of 60° C. and 58° C., respectively, may also be used.

According to one particular embodiment of the invention, the semicrystalline polymers used do not comprise any carboxylic groups.

The polymer(s) used and the amount of this (these) polymer(s) are chosen according to the desired finality of the composition and as a function of the particular application envisaged. In general, the composition of the invention preferably comprises at least one semicrystalline polymer chosen from semicrystalline polymers with a melting point ranging from 50 to 70° C. and semicrystalline polymers with a melting point ranging from 30 to 50° C., and mixtures thereof.

When the composition of the invention is in the form of a cream, i.e. a soft product as opposed to a solid product, the polymer used may preferably be chosen from those described in Examples 1 and 2 of document U.S. Pat. No. 5,519,063 or EP-A-0550745, having a melting point of 40° C. and 38° C., respectively.

When the composition is solid, according to one preferred embodiment of the invention, the composition comprises at least one semicrystalline polymer having a Tm ranging from 50 to 70° C. According to one more particular embodiment of the invention, a solid composition comprises at least 2 semicrystalline polymers, i.e. at least one semicrystalline polymer having a Tm ranging from 50° C. to 70° C. and at least one semicrystalline polymer having a Tm ranging from 25° C. to 50° C. and better still from 30° C. to 50° C. The total amount of semicrystalline polymer is then chosen according to the desired hardness of the composition and as a function of the particular application envisaged. This hardness is such that the composition is self-supporting, i.e. it supports itself, remaining in its solid form (for example as a tube) and it does not collapse under its own weight as do creams or liquids, and it can be easily disintegrated to form a satisfactory deposit on the skin and the lips. The hardness of the sticks obtained is measured at 20° C. using a DFGHS 2 tensile testing machine from the company Indelco-Chatillon travelling at a speed of 100 mm/minute. This hardness is expressed as the shear force (expressed in gram-force, gf) required to break a stick 12.7 mm in diameter under these conditions. In the present patent application, the shear force of the composition preferably ranges from 100 to 350 gf, better still from 120 to 250 gf and even better still from 150 to 220 gf.

In practice, the total amount of semicrystalline polymer preferably represents, in % weight, from 0.1% to 50% by weight relative to the total weight of the composition. When the composition is a cream, this amount preferably ranges from 0.5% to 20% by weight and better still from 1% to 10% by weight relative to the total weight of the composition. When the composition is a solid, this amount preferably ranges from 1% to 40% by weight and better still from 5% to 20% by weight relative to the total weight of the composition, this amount preferably being at least 5% by weight relative to the total weight of the composition. In the case of a stick, advantageously, the weight ratio of semicrystalline polymer relative to the oily phase is from 0.20 to 0.60 and better still from 0.25 to 0.50, to obtain a hard stick that disintegrates on contact with the skin or the lips and in particular with a hardness ranging from 100 to 350 gf.

Oily Phase

When the composition is in the form of a W/O emulsion, the oily phase gelled with the semicrystalline polymer constitutes the continuous phase of the emulsion. This oily phase may be present in an amount ranging, for example, from 10% to 95% by weight, preferably from 10% to 80% by weight, better still from 15% to 70% by weight and even better still from 20% to 60% by weight relative to the total weight of the composition.

This oily phase comprises at least one oil, especially a cosmetic oil, and it may contain several oils and optionally one or more other fatty substances.

Examples of oils that may be used in the composition of the invention include:
- hydrocarbon-based oils of animal origin, such as perhydrosqualene;
- hydrocarbon-based oils of plant origin, such as liquid triglycerides of fatty acids containing from 4 to 10 carbon atoms, for instance heptanoic or octanoic acid triglycerides or alternatively, for example, sunflower oil, corn oil, soybean oil, marrow oil, grapeseed oil, sesame oil, hazelnut oil, apricot oil, macadamia oil, arara oil, sunflower oil, castor oil, avocado oil, caprylic/capric acid triglycerides, for instance those sold by the company Stearineries Dubois or those sold under the names Miglyol 810,812 and 818 by the company Dynamit Nobel, jojoba oil or karite butter oil;
- synthetic esters and synthetic ethers, especially of fatty acids, for instance oils of formulae $R^1COOR^2$ and $R^1OR^2$ in which $R^1$ represents a fatty acid residue containing from 8 to 29 carbon atoms, and $R^2$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

linear or branched hydrocarbons of mineral or synthetic origin, such as volatile or non-volatile liquid paraffins, and derivatives thereof, petroleum jelly, polydecenes, and hydrogenated polyisobutene such as Parleam® oil;

fatty alcohols containing from 8 to 26 carbon atoms, for instance cetyl alcohol, stearyl alcohol and a mixture thereof (cetearyl alcohol), octyldodecanol, 2-butyloctanol, 2-hexyldecanol, 2-undecylpentadecanol, oleyl alcohol or linoleyl alcohol;

partially hydrocarbon-based and/or silicone-based fluoro oils, for instance those described in document JP-A-2295912;

silicone oils, for instance volatile or non-volatile polymethylsiloxanes (PDMSs) containing a linear or cyclic silicone chain, that are liquid or pasty at room temperature, especially volatile silicone oils such as cyclopolydimethylsiloxanes (cyclomethicones), for instance cyclohexasiloxane (or cyclohexamethicone) and cyclopentadimethylsiloxane (or cyclopentamethicone) and mixtures thereof; polydimethylsiloxanes comprising alkyl, alkoxy or phenyl groups, that are pendent or at the end of a silicone chain, these groups containing from 2 to 24 carbon atoms; phenylsilicones, for instance phenyltrimethicones, phenyldimethicones, phenyltrimethylsiloxydiphenylsiloxanes, diphenyldimethicones, diphenylmethyldiphenyltrisiloxanes, 2-phenylethyltrimethylsiloxysilicates and polymethylphenylsiloxanes;

mixtures thereof.

In the list of oils mentioned above, the term "hydrocarbon-based oil" means any oil mainly comprising carbon and hydrogen atoms, and optionally ester, ether, fluoro, carboxylic acid and/or alcohol groups.

Other fatty substances that may be present in the oily phase include, for example, fatty acids containing from 8 to 30 carbon atoms, for instance stearic acid, lauric acid, palmitic acid and oleic acid; waxes; gums such as silicone gums (dimethiconol); silicone resins such as trifluoromethyl-C1-4-alkyldimethicone and trifluoropropyldimethicone; silicone elastomers, for instance the products sold under the names "KSG" by the company Shin-Etsu, under the names "Trefil", "BY29" or "EPSX" by the company Dow Corning, or under the name "Gransil" by the company Grant Industries; and also silicone elastomers comprising one or more oxyalkylenated and especially oxyethylenated chains, such as the product sold under the name "KSG 21" by the company Shin-Etsu; and mixtures thereof These fatty substances may be chosen in a varied manner by a person skilled in the art in order to prepare a composition having the desired properties, for example in terms of consistency or texture, in view of this disclosure.

When the composition according to the invention is intended for removing makeup from the skin, the oily phase of the composition according to the invention preferably contains at least one makeup-removing oil, and especially an oil chosen from fatty acid esters containing at least 12 carbon atoms. The makeup-removing oil may be chosen especially from the group comprising 2-ethylhexyl palmitate (or octyl palmitate), 2-ethylhexyl myristate (or octyl myristate), isopropyl palmitate, isopropyl myristate, diisopropyl adipate, dioctyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethyl hexyl octanoate, 2-ethylhexyl caprate/caprylate, methyl palmitate, butyl myristate, isobutyl myristate, ethyl palmitate, isohexyl laurate, hexyl laurate and isopropyl isostearate, and mixtures thereof. The amount of makeup-removing oil(s) may constitute all the oil of the oily phase or a portion thereof. It preferably constitutes at least 10% by weight relative to the total weight of the composition. This amount can range, for example, from 10% to 95%, preferably from 10% to 80% and better still from 10% to 60% by weight, relative to the total weight of the composition.

Moreover, a wax may especially be incorporated in the solid compositions. Included are standard waxes such as those generally used in cosmetics and dermatology; they are preferably of natural origin, for instance beeswax, candelilla wax, ouricoury wax, Japan wax, cork fibre wax, sugar cane wax, paraffin wax, lignite wax, microcrystalline waxes with a melting point >50° C., lanolin wax, montan wax, ozokerites, hydrogenated oils, for instance hydrogenated jojoba oil (CTFA name: hydrogenated jojoba oil), and also waxes of synthetic origin, for instance the polyethylene waxes obtained from the polymerization of ethylene, the waxes obtained by Fischer-Tropsch synthesis with a melting point >50° C., fatty acid esters of glycerides that are solid at 50° C., and silicone waxes, for instance alkyl, alkoxy and/or esters of poly(di)methylsiloxane that are solid at 50° C.

According to one particular embodiment of the invention, when the composition is in solid form, it preferably contains at least one wax chosen from polyethylene waxes and hydrogenated jojoba waxes, and mixtures thereof. Examples of waxes that may be used include a polyethylene wax such as the product sold under the name Perfomalene 655 by the company New Phase Technologies, which has a melting point of 93° C., and the hydrogenated jojoba oil sold by Desert Whale, which has a melting point of 70° C.

Emulsifier

The emulsifier in the composition according to the invention has an HLB (hydrophilic-lipophilic balance) value ranging from 1 to 8, including 2, 3, 4, 5, 6, and 7.

The emulsifier may be chosen, for example, from silicone emulsifiers, alkylpolyglycosides (APG), nonionic emulsifiers derived from fatty acid and from polyol, and polyolefins containing a succinic end group, and mixtures thereof.

Useful silicone emulsifiers that may form part of the composition according to the invention include dimethicone copolyols and alkyldimethicone copolyols. An example of a dimethicone copolyol that may be mentioned is the mixture of dimethicone copolyol and of dimethicone (polydimethylsiloxane) (10/90) sold by the company Dow Corning under the name DC3225C. According to one preferred embodiment of the invention, the silicone emulsifier used is an alkyldimethicone copolyol having an alkyl radical containing from 10 to 22 carbon atoms, such as cetyldimethicone copolyol, for instance the product sold under the name Abil EM-90 by the company Goldschmidt, and such as the mixture of cetyldimethicone copolyol, of polyglyceryl isostearate (4 mol) and of hexyl laurate, sold under the name Abil WE 09 by the company Goldschmidt; lauryldimethicone copolyol, and for example the mixture of about 91% of lauryldimethicone copolyol and of about 9% of isostearyl alcohol, sold under the name Q2-5200 by the company Dow Corning, and mixtures thereof.

Useful nonionic emulsifiers derived from fatty acid and from polyol include fatty acid esters of polyols, the fatty acid especially containing a C8-C24 alkyl chain, and the polyols being, for example, glycerol and sorbitan. Fatty acid esters of polyols that may especially be mentioned include isostearic acid esters of polyols, stearic acid esters of polyols, and mixtures thereof, in particular isostearic acid esters of glycerol and/or of sorbitan, for example polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and the mixture of sorbitan isostearate and of polyglyceryl isostearate (3 mol) sold under the name Arlacel 1690 by the company Uniqema, and mixtures thereof.

The emulsifier may also be chosen from alkylpolyglycosides with an HLB value of less than 7, for example those represented by the general formula (I) below:

$$R\text{—}O\text{—}(G)_x \qquad (I)$$

in which R represents a branched and/or unsaturated alkyl radical containing from 14 to 24 carbon atoms, G represents a reduced sugar containing 5 or 6 carbon atoms, and x denotes a value ranging from 1 to 10 and preferably from 1 to 4, and G especially denotes glucose, fructose or galactose.

The unsaturated alkyl radical may comprise one or more ethylenic unsaturations, and in particular one or two ethylenic unsaturations.

Useful alkylpolyglycosides of this type include alkylpolyglucosides (G=glucose in formula (I)), and especially the compounds of formula (I) in which R more particularly represents an oleyl radical (unsaturated C18 radical) or an isostearyl radical (saturated C18 radical), G denotes glucose, x is a value ranging from 1 to 2, especially isostearylglucoside or oleylglucoside, and mixtures thereof. This alkylpolyglucoside may be used as a mixture with a co-emulsifier, more especially with a fatty alcohol and especially a fatty alcohol having the same fatty chain as that of the alkylpolyglucoside, i.e. containing from 14 to 24 carbon atoms and having a branched and/or unsaturated chain, and for example isostearyl alcohol when the alkylpolyglucoside is isostearylglucoside, and oleyl alcohol when the alkylpolyglucoside is oleylglucoside, optionally in the form of a self-emulsifying composition, as described, for example, in document WO-A-92/06778. The mixture of isostearylglucoside and of isostearyl alcohol sold under the name Montanov WO 18 by the company SEPPIC may be used, for example.

Polyolefins containing a succinic end group that may especially be mentioned include polyisobutylenes containing an esterified succinic end group and salts thereof, especially the diethanolamine salts, such as the products sold under the names Lubrizol 2724, Lubrizol 2722 and Lubrizol 5603 by the company Lubrizol.

The emulsifier is used in any amount, and is preferably used in an amount ranging, for example, from 0.1% to 20% by weight, more preferably from 0.5% to 10% by weight and better still from 0.5% to 5% by weight relative to the total weight of the composition.

The emulsifier is preferably introduced into the oily phase of the emulsion.

Aqueous Phase

The aqueous phase of the composition of the invention is not limited and generally represents from 5% to 90% by weight and preferably from 20% to 60% by weight, relative to the total weight of the composition. Besides water, it may contain solvents such as primary alcohols containing from 1 to 6 carbon atoms, for instance ethanol, or polyols, for instance butylene glycol, glycerol, sorbitol, hexylene glycol, propylene glycol and isoprene glycol, or sugars, for instance glucose or fructose. The solvent(s) may be present in any amount such as an amount ranging from 0.1% to 30% by weight relative to the total weight of the composition.

Organic Powder

In the present patent application, the term "organic powder" means any solid that is insoluble in the medium at room temperature (25° C.).

Useful organic powders that may be used in the composition of the invention include polyamide particles and especially those sold under the name Orgasol by the company Atochem; polyethylene powders; microspheres based on acrylic copolymers, such as those made of ethylene glycol dimethacrylate/lauryl methacrylate copolymer, sold by the company Dow Corning under the name Polytrap; polymethyl methacrylate microspheres, sold under the name Microsphere M-100 by the company Matsumoto or under the name Covabead LH85 by the company Wackherr; ethylene-acrylate copolymer powders, for instance those sold under the name Flobeads by the company Sumitomo Seika Chemicals; expanded powders such as hollow microspheres and especially microspheres formed from a terpolymer of vinylidene chloride, of acrylonitrile and of methacrylate and sold under the name Expancel by the company Kemanord Plast under the references 551 DE 12 (particle size of about 12 µm and density of 40 kg/m$^3$), 551 DE 20 (particle size of about 30 µm and a density of 65 kg/m$^3$) and 551 DE 50 (particle size of about 40 µm), or the microspheres sold under the name Micropearl F 80 ED by the company Matsumoto; powders of natural organic materials such as starch powders, especially of corn starch, wheat starch or rice starch, which may or may not be crosslinked, such as the starch powder crosslinked with octenylsuccinate anhydride, sold under the name Dry-Flo by the company National Starch; silicone resin microbeads such as those sold under the name Tospearl by the company Toshiba Silicone, especially Tospearl 240; amino acid powders such as the lauroyllysine powder sold under the name Amihope LL-11 by the company Ajinomoto; particles of wax microdispersion, which preferably have mean sizes of less than 1 µm and especially ranging from 0.02 µm to 1 µm, and which consist essentially of a wax or a mixture of waxes, such as the products sold under the name Aquacer by the company Byk Cera, and especially: Aquacer 520 (mixture of synthetic and natural waxes), Aquacer 514 or 513 (polyethylene wax), Aquacer 511 (polymer wax), or such as the products sold under the name Jonwax 120 by the company Johnson Polymer (mixture of polyethylene wax and paraffin wax) and under the name Ceraflour 961 by the company Byk Cera (micronized modified polyethylene wax); and mixtures thereof. The organic powder(s) may be present in any amount including, for example, in an amount ranging from 0.1% to 20% by weight and preferably from 0.5% to 10% by weight relative to the total weight of the composition.

One or more mineral fillers may be added to the invention composition, such as, for example, silica; metal oxides such as titanium dioxide or zinc oxide; mica; and mixtures thereof. The amount of mineral filler(s) may range, for example, from 0.05% to 20% by weight and better still from 0.1% to 10% by weight, relative to the total weight of the composition.

According to one preferred embodiment of the invention, the organic powder(s) is(are) added to the composition after mixing together the aqueous and oily phases.

Additives

The composition of the invention may also comprise any additive commonly used in the field under consideration, for example chosen from thickeners, gelling agents, dyestuffs, antioxidants, essential oils, preserving agents, fragrances, dispersants, neutralizers, lipophilic or hydrophilic active agents, electrolytes such as magnesium sulphate or sodium chloride, and mixtures thereof. These additives may be present in the composition in the amounts generally used for example in the fields of cosmetics and dermatology and especially in a proportion of from 0.01% to 50% and better still from 0.1% to 20%, relative to the total weight of the composition. Water may preferably represent up to 90% relative to the total weight of the composition.

Examples of useful active agents include moisturizers, and for example protein hydrolysates and polyols such as glycerol, glycols, for instance polyethylene glycols, and sugar derivatives; natural extracts; procyannidol oligomers; vitamins, for instance vitamin E (tocopherol) and its derivatives (for example the acetate), vitamin A (retinol) and its derivatives (for example retinyl palmitate), vitamin C (ascorbic acid) and its derivatives (for example ascorbyl palmitate), the derivatives of these vitamins especially being esters, including the palmitate and the acetate; essential fatty acids; sphingolipids and ceramides; self-tanning compounds such as DHA (dihydroxyacetone); sunscreens such as, for example, octyl methoxycinnamate (Parsol MCX), 3-benzophenone (Uvinul M40), butylmethoxydibenzoylmethane (Parsol 1789); urea; depigmenting agents such as kojic acid and caffeic acid; β-hydroxy acids such as salicylic acid and its derivatives; α-hydroxy acids such as lactic acid, citric acid and glycolic acid; retinoids such as retinol and its esters, retinal and carotenoids; and mixtures thereof.

Gelling agents that may preferably be used include hydrophilic gelling agents such as carboxyvinyl polymers, for instance carbomers; polyacrylamides and polymers and copolymers of 2-acrylamido-2-methyl-propanesulphonic acid, optionally crosslinked and/or neutralized, for instance poly(2-acrylamido-2-methylpropanesulphonic acid) sold by the company Clariant under the trade name "Hostacerin AMPS" (CTFA name: ammonium polyacryldimethyltauramide); or the acrylamide/sodium 2-acrylamidomethylpropanesulphonate copolymer as a 40% inverse emulsion in polysorbate, sold under the name Simulgel 600 by the company SEPPIC; polysaccharides such as xanthan gum; and mixtures thereof.

When they are present, these gelling agents are generally preferably used at concentrations ranging from 0.05% to 7% and more preferably from 0.1% to 5% by weight of active material, relative to the total weight of the composition.

Needless to say, a person skilled in the art will prefaerably take care to select the optional additional additives and/or the amount thereof such that the advantageous properties of the composition according to the invention are not, or are not substantially, adversely affected by the envisaged addition.

The composition according to the invention may be manufactured by known processes generally used in cosmetics or dermatology, within the skill of the ordinary artisan in view of this discosure. It may be manufactured by a process that consists in heating the polymer at least to its melting point (Tm), adding the emulsifier(s) and other constituents of the oily phase thereto, preparing the aqueous phase at a temperature above the melting point (Tm) of the polymer and introducing the aqueous phase into the oily phase with stirring, and then adding the powder(s) under hot or cold conditions, depending on the desired composition.

The compositions in cream form are cooled without further modification, while the solid compositions are generally, before cooling, cast in a suitable mould, for instance a stick mould, or poured directly into the packaging articles (especially a case or dish).

The composition according to the invention finds its application in numerous treatments, including cosmetic treatments, for the skin, including the scalp, the hair, the nails and/or mucous membranes. It may be used for any skin type, and in particular for caring for, treating, cleansing and/or protecting, especially against sunlight, the skin, the hair and/or the lips or mucous membranes, and for making up the skin and/or the lips, and also for the preparation of a cream for treating the skin, more particularly greasy skin.

The composition of the invention may also constitute a makeup composition after adding pigments and/or colorants, and it may also constitute a very effective makeup base (cream applied before the foundation or powder) which allows adhesion of the makeup coat consisting of the foundation or powder.

Thus, a subject of the present invention is the use of a composition as defined above, for treating, protecting, caring for, removing makeup from and/or cleansing the skin, the lips and/or the hair, and/or for making up the skin and/or the lips.

Another subject of the present invention is a process for treating the skin, including the scalp, the hair and/or the lips, characterized in that a composition as defined above is applied to the skin, the hair and/or the lips.

Another subject of the invention is the use of the composition as defined above for the manufacture of a cream for treating greasy skin.

The composition of the invention may also advantageously constitute a makeup-removing or cleansing composition for the skin, the lips and the integuments, which may especially be in solid form, for example in the form of a stick (or tube) or in cast form. This composition is capable of removing makeup from or cleansing the skin, the lips or the integuments of human beings.

Another subject of the invention is a process for removing makeup from or for cleansing the skin, the lips and the integuments, which comprises applying the composition, especially the solid cosmetic composition as defined above, to the skin, the lips or the integuments. This solid composition may more especially be a stick, that is easy to use and allows a novel makeup-removing action.

The invention is illustrated in greater detail in the examples that follow. The amounts are given as percentages by mass (weight).

I) EXAMPLES OF THE MANUFACTURE OF SEMICRYSTALLINE POLYMERS

Example 1

Acidic Polymer with a Melting Point of 40° C.

120 g of Parleam® oil (mineral oil) are placed in a 1 litre reactor fitted with a central stirrer with a paddle, a condenser and a thermometer, and the oil is heated from room temperature to 80° C. over 45 minutes. At 80° C., the mixture $C_1$ below is introduced over 2 hours:

40 g of cyclohexane+4 g of Triganox 141 [2,5-bis(2-ethylhexanoylperoxy)-2,5-dimethylhexane].

Thirty minutes after the start of addition of mixture $C_1$, the mixture $C_2$ consisting of:

190 g of stearyl acrylate+10 g of acrylic acid+400 g of cyclohexane is introduced over 1 hour 30 min.

At the end of the two additions, the resulting mixture is stirred for a further 3 hours at 80° C., and all of the cyclohexane present in the reaction medium is then distilled off at atmospheric pressure.

The polymer containing 60% by weight of active material in the Parleam® oil is thus obtained.

Its weight-average molecular mass $M_W$ is 35,000, expressed as polystyrene equivalent, and its melting point Tm is 40° C.±1° C., measured by DSC.

Example 2

Basic Polymer with a Melting Point of 38° C.

The same procedure as in Example 1 is applied, except that N-vinylpyrrolidone is used instead of acrylic acid.

The polymer obtained is at 60% by weight of active material in the Parleam® oil, its weight-average molecular mass $M_W$ is 38,000 and its Tm is 38° C.

Example 3

Acidic Polymer with a Melting Point of 60° C.

The same procedure as in Example 1 is applied, except that behenyl acrylate is used instead of stearyl acrylate. The polymer obtained is at 60% by weight of active material in the Parleam® oil. Its weight-average molecular mass $M_W$ is 42 000 and its Tm is 60° C.

Example 4

Basic Polymer with a Melting Point of 58° C.

The same procedure as in Example 2 is applied, except that behenyl acrylate is used instead of stearyl acrylate. The polymer obtained is at 60% by weight of active material in the Parleam® oil. Its $M_W$ is 45 000 and its Tm is 58° C.

II) COMPOSITION EXAMPLES

Example 5

Care Cream

| Oily phase | |
| --- | --- |
| Stearyl acrylate/N-vinylpyrrolidone copolymer at 60% active material in Parleam ® oil according to Example 2 | 2% |
| Isohexadecane | 15% |
| Silicone oil | 10% |
| Cetyldimethicone copolyol (Abil EM90 from the company Goldschmidt) | 1.5% |
| Polyglyceryl isostearate (Isolan GI 34) | 0.5% |
| Aqueous phase | |
| Glycerol | 3% |
| Magnesium sulphate | 0.7% |
| Preserving agents | qs % |
| Demineralized water | qs 100% |
| Organic powder | |
| Starch powder | 3% |

Procedure: Each of the phases is heated until hot (>70° C.) and the aqueous phase is then dispersed in the oily phase with stirring. The mixture is cooled to 40° C. and the starch powder is added.

A silky white care cream that is soft and slippery when applied is obtained. The appearance in the jar is compact, but when handled, the cream melts to spread easily with a sensation of freshness. The skin becomes softer, more silky and better moisturized.

Example 6

Care Cream

| Oily phase | |
| --- | --- |
| Stearyl acrylate/acrylic acid copolymer at 60% active material in Parleam ® oil according to Example 1 | 2% |
| Isohexadecane | 15% |
| Silicone oil | 8% |
| Mineral oil | 2% |
| Cetyldimethicone copolyol (Abil EM90 from the company Goldschmidt) | 1.5% |
| Polyglyceryl isostearate (Isolan GI 34) | 0.5% |
| Mica-titanium oxide (Flamenco Red 420 C from the company Engelhard) | 1% |
| Aqueous phase | |
| Glycerol | 3% |
| Magnesium sulphate | 0.7% |
| Preserving agents | qs % |
| Demineralized water | qs 100% |
| Organic powder | |
| Vinylidene chloride/acrylonitrile/methacrylate microspheres (Expancel 551 DE) | 0.5% |

Procedure: Each of the phases is heated until hot (>70° C.) and the aqueous phase is then dispersed in the oily phase with stirring. The mixture is cooled to 40° C. and the organic powder is added.

A beautiful nacreous cream that is soft and slippery when applied is obtained. This cream spreads easily on the skin, giving a sensation of freshness and leaving the skin soft and satiny.

Example 7

Care Cream

| Oily phase | |
| --- | --- |
| Stearyl acrylate/N-vinylpyrrolidone copolymer at 60% active material in Parleam ® oil according to Example 2 | 3% |
| Isohexadecane | 8% |
| Volatile silicone oil | 3% |
| Refined plant perhydrosqualene | 5% |
| Sorbitan isostearate/polyglyceryl isostearate (3 mol) (Arlacel 1690) | 4% |
| Polyglyceryl isostearate (Isolan GI 34) | 0.5% |
| Aqueous phase | |
| Glycerol | 3% |
| Magnesium sulphate | 0.7% |
| Preserving agents | qs % |
| Demineralized water | qs 100% |

-continued

| Organic powder | |
|---|---|
| Polyamide powder (Orgasol 2002 NAT COS) | 3% |
| Fragrance | 0.5% |

Procedure: Each of the phases is heated until hot (>70° C.) and the aqueous phase is then dispersed in the oily phase with stirring. The mixture is cooled to 40° C. and the polyamide powder and fragrance are added.

A beautiful rich and comfortable white cream that is particularly suitable for normal to dry skin is obtained.

Example 8

Complexion Cream

| Oily phase | |
|---|---|
| Stearyl acrylate/N-vinylpyrrolidone at 60% active material in Parleam ® oil according to Example 2 | 2% |
| Isohexadecane | 10% |
| Volatile silicone oil | 7% |
| Isononyl isononanoate | 5% |
| Sweet almond oil | 0.5% |
| Mixture of isostearylglucoside and of isostearyl alcohol (Montanov WO18 from SEPPIC) | 5% |
| Polyglyceryl isostearate (Isolan GI34 from Goldschmidt) | 0.5% |
| Coated iron oxides (brown, yellow and black) | 5% |
| Aqueous phase | |
| Glycerol | 3% |
| Magnesium sulphate | 0.7% |
| Preserving agents | qs % |
| Demineralized water | qs 100% |
| Organic powders | |
| Polyamide powder (Orgasol 2002 NAT COS) | 6% |
| Polyethylene powder | 4% |
| Fragrance | 0.5% |

Procedure: The oily phase and the aqueous phase are heated to about 70° C. and the aqueous phase is then dispersed in the oily phase with stirring. The mixture is cooled to 50° C. and the organic powder is then added. The resulting mixture is cooled with very gentle stirring.

A beautiful coloured cream, which feels soft and non-greasy, which spreads easily and which makes the skin smooth and homogenizes the complexion is obtained.

Example 9

Makeup-removing Stick

| Oily phase | |
|---|---|
| Stearyl acrylate/acrylic acid copolymer at 60% active material in Parleam oil according to Example 1 | 12% |
| Behenyl acrylate/acrylic acid copolymer at 60% active material in Parleam oil according to Example 3 | 10% |

-continued

| Isopropyl palmitate | 45% |
|---|---|
| Mixture of cetyldimethicone copolyol, polyglyceryl isostearate (4 mol) and hexyl laurate (Abil WE 09 from the company Goldschmidt) | 5% |
| Acrylate copolymer (Expancel 551 DE 20D60 from the company Expancel) | 0.1% |
| Aqueous phase | |
| Glycerol | 5% |
| Magnesium sulphate | 0.7% |
| Preserving agents | 0.8% |
| Demineralized water | qs 100% |

Procedure: The oily phase is heated to 80° C. The aqueous phase is prepared at 80° C. and is added to the oily phase with stirring.

A homogeneous stick with a fondant feel, which spreads well and is not sticky, is obtained. This stick allows good makeup-removal from the skin.

Example 10

Makeup-removing Stick

| Oily phase | |
|---|---|
| Stearyl acrylate/acrylic acid copolymer at 60% active material in Parleam oil according to Example 1 | 12% |
| Behenyl acrylate/acrylic acid copolymer at 60% active material in Parleam oil according to Example 3 | 10% |
| Isoparaffin | 15% |
| Isopropyl palmitate | 30% |
| Mixture of cetyldimethicone copolyol, polyglyceryl isostearate (4 mol) and hexyl laurate (Abil WE 09 from the company Goldschmidt) | 5% |
| Acrylate copolymer (Expancel 551 DE 20D60 from the company Expancel) | 0.8% |
| Aqueous phase | |
| Glycerol | 5% |
| Magnesium sulphate | 0.7% |
| Preserving agents | 0.8% |
| Demineralized water | qs 100% |

Procedure: The oily phase is heated to 80° C. The aqueous phase is prepared at 80° C. and is added to the oily phase with stirring.

A homogeneous stick with a fondant feel, which is soft, slippery and non-sticky when applied, is obtained. This stick allows efficient and gentle makeup-removal from the skin.

Example 11

Makeup-Removing Stick

| Oily phase | |
|---|---|
| Hydrogenated jojoba oil from the company Desert Whale (melting point 70° C.) | 7% |
| Polyethylene wax (Perfomalene 655) | 2% |

-continued

| | |
|---|---|
| Behenyl acrylate/acrylic acid copolymer at 60% active material in Parleam according to Example 3 | 8% |
| Mixture of cetyldimethicone copolyol, polyglyceryl isostearate (4 mol) and hexyl laurate (Abil WE 09 from the company Goldschmidt) | 5% |
| Isopropyl palmitate | 45% |
| Nylon-12 (Orgasol 2002 EXD NAT COS from the company Atochem) | 1.5% |
| Aqueous phase | |
| Glycerol | 5% |
| Magnesium sulphate | 0.7% |
| Preserving agents | 0.8% |
| Demineralized water | qs 100% |

Procedure: The oily phase is heated to 80° C. The aqueous phase is prepared at 80° C. and added to the oily phase with stirring.

A homogeneous stick of rich texture, which is soft when applied and which allows good makeup-removal of the skin, is obtained.

Example 12

Makeup-Removing Stick

| | |
|---|---|
| Oily phase | |
| Hydrogenated jojoba oil from the company Desert Whale (melting point 70° C.) | 7% |
| Polyethylene wax (Perfomalene 655) | 2% |
| Behenyl acrylate/acrylic acid copolymer at 60% active material in Parleam according to Example 3 | 8% |
| Mixture of cetyldimethicone copolyol, polyglyceryl isostearate (4 mol) and hexyl laurate (Abil WE 09 from the company Goldschmidt) | 5% |
| Isopropyl palmitate | 39% |
| Silicone oil (DC 200 Fluid - 5 cSt from the company Dow Corning) | 5% |
| Apricot oil | 1% |
| Nylon-12 (Orgasol 2002 EXD NAT COS from the company Atochem) | 1.5% |
| Aqueous phase | |
| Glycerol | 5% |
| Magnesium sulphate | 0.7% |
| Preserving agents | 0.8% |
| Demineralized water | qs 100% |

Procedure: The oily phase is heated to 80° C. The aqueous phase is prepared at 80° C. and added to the oily phase with stirring.

A homogeneous stick with a rich and fondant texture, which is very comfortable to apply and which allows gentle and efficient makeup-removal of the skin, is obtained.

Example 13

Two-gel Makeup-removing Stick

| | |
|---|---|
| Oily phase | |
| Stearyl acrylate/acrylic acid copolymer at 60% active material in Parleam oil according to Example 1 | 12% |
| Behenyl acrylate/acrylic acid copolymer at 60% active material in Parleam oil according to Example 3 | 10% |
| Isopropyl palmitate | 45% |
| Mixture of cetyldimethicone copolyol, polyglyceryl isostearate (4 mol) and hexyl laurate (Abil WE 09 from the company Goldschmidt) | 5% |
| Nylon-12 (Orgasol 2002 EXD NAT COS from the company Atochem) | 1.5% |
| Aqueous phase | |
| Glycerol | 5% |
| Ammonium polyacryloyldimethyltaurate (Hostacerin AMPS) | 0.5% |
| Preserving agents | 0.8% |
| Demineralized water | qs 100% |

Procedure: The oily phase is heated to 80° C. The aqueous phase is prepared at 80° C. and added to the oily phase with stirring.

A homogeneous stick with a texture that is both fondant and fresh, which is allows good makeup-removal of the skin, is obtained.

Example 14

This example is performed by replacing in Example 9 the copolymer of Example 1 with the copolymer of Example 2 based on stearyl acrylate and on N-vinylpyrrolidone.

The above description of the invention sets forth the manner and process of making and using it such that it enables any person skilled in this art to make and use the same, specifically including the making and using of the following preferred embodiments and those set out in the claims, all of which make up a part of this description:

a composition for topical application, comprising an aqueous phase dispersed in an oily phase, characterized in that it contains at least one organic powder and at least one emulsifier with an HLB value ranging from 1 to 8, and in that the oily phase contains at least one semicrystalline polymer that is solid at room temperature and that has a melting point of less than 70° C., the said polymer comprising a) a polymer skeleton and b) at least one crystallizable organic side chain and/or a crystallizable organic sequence forming part of the said polymer skeleton, the said polymer having a number-average molecular mass of greater than 2,000, the use of such a composition for treating, protecting, caring for, removing makeup from and/or cleansing the skin, the lips and/or the hair, and/or for making up the skin and/or the lips, a process for treating the skin, including the scalp, the hair and/or the lips, characterized in that such a composition is applied to the skin, the hair and/or the lips.

a process for removing makeup from or for cleansing the skin, the lips and the integuments, which comprises applying such a composition to the skin, the lips or the integuments.

the use of such a composition for the manufacture of a cream for treating greasy skin.

All references, documents, brochures, texts, articles, patents, applications, etc. mentioned above are incorporated herein by reference. Where a numerical limit or range is stated, all values and subranges within these stated ranges or limits are expressly included as if specifically written out.

The invention claimed is:

1. A composition comprising an aqueous phase dispersed in an oily phase, at least one organic powder and at least one emulsifier with an HLB value of 1 to 8 selected from the group consisting of silicone emulsifiers, nonionic emulsifiers derived from fatty acid and from polyol, alkpolyglycosides, and polyolefins containing a succinic end group; and mixtures thereof, wherein the aqueous phase comprises water and the oily phase comprises at least one oil and at least one semicrystalline polymer that is solid at room temperature and that has a melting point of less than 70° C., said polymer comprising a) a polymer skeleton and b) at least one crystallizable organic side chain and/or at least one crystallizable organic sequence forming part of said polymer skeleton, said polymer having a number-average molecular weight of greater than 2,000.

2. A composition according to claim 1, wherein the polymer has a number-average molecular weight of from 3,000 to 500,000.

3. A composition according to claim 1, wherein the polymer is soluble in the oily phase to at least 1% by weight at a temperature above its melting point.

4. A composition according to claim 1, wherein the polymer has a melting point Tm such that 30° C.≦Tm ≦60° C.

5. A composition according to claim 1, wherein the polymer is selected from the group consisting of:
  block copolymers of polyolefins of controlled crystallization,
  aliphatic or aromatic polyester polycondensates and aliphatic/aromatic copolyesters;
  polymers bearing at least one crystallizable side chain, and polymers bearing in the skeleton at least one crystallizable sequence,
  polymers bearing at least one crystallizable side chain containing at least one fluoro group,
  and mixtures thereof.

6. A composition according to claim 1, wherein the polymer is selected from the group consisting of homopolymers and copolymers comprising from 50% to 100% by weight of units resulting from polymerization of one or more monomers bearing crystallizable hydrophobic side chain(s).

7. A composition according to claim 1, wherein the polymer is selected from the group consisting of homopolymers and copolymers resulting from the polymerization of at least one monomer containing crystallizable chain(s) of formula X:

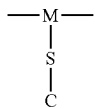

in which M represents an atom of the polymer skeleton, S represents a spacer and C represents a crystallizable group.

8. A composition according to claim 1, wherein the polymer is selected from the group consisting of homopolymers and copolymers resulting from the polymerization of at least one monomer containing a crystallizable chain chosen from saturated $C_{14}$-$C_{24}$ alkyl (meth)acrylates, $C_{11}$-$C_{15}$ perfluoroalkyl (meth)acrylates, $C_{14}$ to $C_{24}$ N-alkyl(meth)acrylamides with or without a fluorine atom, vinyl esters containing $C_{14}$ to $C_{24}$ alkyl or perfluoroalkyl chains, vinyl ethers containing $C_{14}$ to $C_{24}$ alkyl or perfluoroalkyl chains, $C_{14}$ to $C_{24}$ α-olefins, and para-alkylstyrenes with an alkyl group containing from 12 to 24 carbon atoms, and mixtures thereof.

9. A composition according to claim 1, wherein the polymer is selected from the group consisting of copolymers resulting from the polymerization of at least one monomer containing a crystallizable chain chosen from saturated $C_{14}$-$C_{24}$ alkyl (meth)acrylates, $C_{11}$-$C_{15}$ perfluoroalkyl (meth)acrylates, $C_{14}$ to $C_{24}$ N-alkyl(meth)acrylamides with or without a fluorine atom, vinyl esters containing $C_{14}$ to $C_{24}$ alkyl or perfluoroalkyl chains, vinyl ethers containing $C_{14}$ to $C_{24}$ alkyl or perfluoroalkyl chains, $C_{14}$ to $C_{24}$ α-olefins, and para-alkylstyrenes with an alkyl-group containing from 12 to 24 carbon atoms, with at least one optionally fluorinated $C_1$ to $C_{10}$ monocarboxylic acid ester or amide, and mixtures thereof.

10. A composition according to claim 1, wherein the polymer is selected from the group consisting of $C_{14}$ to $C_{24}$ alkyl (meth)acrylate or alkyl(meth)acrylamide homopolymers; copolymers of these monomers with a hydrophilic monomer; and mixtures thereof.

11. A composition according to claim 1, wherein the polymer is selected from the group consisting of copolymers of alkyl (meth)acrylate or of alkyl(meth)acrylamide with a $C_{14}$ to $C_{24}$ alkyl group, with N-vinylpyrrolidone, hydroxyethyl (meth)acrylate or acrylic acid; or mixtures thereof.

12. A composition according to claim 1, wherein the polymer is obtained from a monomer containing a crystallizable chain chosen from saturated $C_{14}$-$C_{22}$ alkyl (meth)acrylates.

13. A composition according to claim 1, wherein the composition comprises at least one semicrystalline polymer selected from the group consisting of semicrystalline polymers with a melting point of 50 to 70° C. and semicrystalline polymers with a melting point of 30 to 50° C., and mixtures thereof.

14. A composition according to claim 1, wherein the polymer represents from 0.1% to 50% by weight relative to the total weight of the composition.

15. A composition according to claim 1, wherein the oily phase represents from 10% to 95% by weight relative to the total weight of the composition.

16. A composition according to claim 1, wherein the oily phase comprises at least one oil selected from the group consisting of hydrocarbon-based oils of animal origin, hydrocarbon-based oils of plant origin, synthetic esters and ethers, linear or branched hydrocarbons of mineral or synthetic origin, fatty alcohols containing from 8 to 26 carbon atoms, partially hydrocarbon-based and/or silicone-based fluoro oils, and silicone oils, and mixtures thereof.

17. A composition according to claim 1, wherein the oily phase comprises at least one oil selected from the group consisting of fatty acid esters containing at least 12 carbon atoms.

18. A composition according to claim 1, comprising a silicone emulsifier selected from the group consisting of dimethicone copolyols and alkyldimethicone copolyols.

19. A composition according to claim 1, comprising an emulsifier selected from the group consisting of alkylpolyglycosides represented by formula (I) below:

$$R—O—(G)_x \quad (I)$$

in which R represents a branched and/or unsaturated alkyl radical containing from 14 to 24 carbon atoms, G represents a reduced sugar containing 5 or 6 carbon atoms, and x denotes a value ranging from 1 to 10, and G denotes glucose, fructose or galactose.

20. A composition according to claim 1, comprising an emulsifier selected from the group consisting of isostearic acid esters of polyols, stearic acid esters of polyols, and mixtures thereof.

21. A composition according to claim 1, wherein the emulsifier is present in an amount of 0.1% to 20% by weight relative to the total weight of the composition.

22. A composition according to claim 1, wherein the organic powder is selected from the group consisting of polyamide particles; polyethylene powders; microspheres comprising an acrylic copolymer; polymethyl methacrylate microspheres; ethylene-acrylate copolymer powders; expanded powders; starch powders; amino acid powders; particles of wax microdispersion; and mixtures thereof.

23. A composition according to claim 1, wherein the organic powder is present in 0.1% to 20% by weight relative to the total weight of the composition.

24. A composition according to claim 1, in the form of a cream.

25. A composition according to claim 1, wherein said composition is in solid form.

26. A composition according to claim 1, wherein said composition is a cosmetic or dermatological composition.

27. A method for treating, protecting, caring for, removing makeup from and/or cleansing the skin, the lips and/or the hair, and/or for making up the skin and/or the lips, comprising applying the composition of claim 1 to the skin, the lips and/or the hair.

28. The method according to claim 27, wherein said composition is a cosmetic composition.

29. The method according to claim 28, wherein said composition is applied to the scalp.

30. A method for removing makeup from or for cleansing the skin, the lips and integuments, which comprises applying a composition according to claim 1 to the skin, the lips or the integuments.

* * * * *

UNITED STATES PATENT AND TRADEMARK OFFICE
CERTIFICATE OF CORRECTION

| | | |
|---|---|---|
| PATENT NO. | : 7,255,870 B2 | Page 1 of 1 |
| APPLICATION NO. | : 10/347338 | |
| DATED | : August 14, 2007 | |
| INVENTOR(S) | : Paula Lennon et al. | |

It is certified that error appears in the above-identified patent and that said Letters Patent is hereby corrected as shown below:

Column 23, line 13, "alkpolyglyco" should read --alkylpolyglyco--.

Signed and Sealed this

First Day of April, 2008

JON W. DUDAS
*Director of the United States Patent and Trademark Office*